United States Patent
Stubbs

(10) Patent No.: US 7,047,075 B2
(45) Date of Patent: May 16, 2006

(54) APPARATUS FOR ACTIVELY MONITORING DEVICE FOR LEAD FIXATION IN IMPLANTABLE TISSUE STIMULATORS

(75) Inventor: Scott R. Stubbs, Maple Grove, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 589 days.

(21) Appl. No.: 10/417,565

(22) Filed: Apr. 17, 2003

(65) Prior Publication Data

US 2004/0210268 A1    Oct. 21, 2004

(51) Int. Cl.
*A61N 1/375* (2006.01)
(52) U.S. Cl. .......................... 607/36; 607/37; 439/489; 439/810
(58) Field of Classification Search .................. 607/36, 607/37; 73/1.13, 1.15; 439/810, 814, 489, 439/490
See application file for complete search history.

(56) References Cited

U.S. PATENT DOCUMENTS

| | | | |
|---|---|---|---|
| 5,626,626 A | 5/1997 | Carson | |
| 5,645,577 A | 7/1997 | Froberg et al. | |
| 5,683,433 A | 11/1997 | Carson | |
| 6,112,121 A | 8/2000 | Paul et al. | |
| 6,165,005 A * | 12/2000 | Mills et al. | 439/489 |
| 6,192,276 B1 * | 2/2001 | Strandberg | 607/36 |
| 6,672,895 B1 * | 1/2004 | Scheiner | 439/491 |
| 6,907,292 B1 * | 6/2005 | Hill | 607/37 |

* cited by examiner

*Primary Examiner*—Robert E. Pezzuto
*Assistant Examiner*—Eric Bertram
(74) *Attorney, Agent, or Firm*—Nikolai & Mersereau, P.A.; Thomas J. Nikolai

(57) ABSTRACT

To provide a positive indication that a medical lead terminal is properly secured within the longitudinal bore in the header of an implantable medical device there is provided a force sensor (strain gauge) positioned within the device's lead receiving bore and cooperating with the lock mechanism to provide an indication of the amount of force being exerted on the lead terminal to retain it in place. The force sensor provides an output signal through the device's feedthrough wires to the electronic circuit contained within a hermetically sealed housing and is compared by a microprocessor to preprogrammed values. The results of the comparison may then be telemetered to an external programmer device for analysis by a physician.

17 Claims, 3 Drawing Sheets

APPARATUS FOR ACTIVELY MONITORING DEVICE FOR LEAD FIXATION IN IMPLANTABLE TISSUE STIMULATORS

BACKGROUND OF THE INVENTION

I. Field of the Invention

This invention relates generally to implantable medical devices of the type including a pulse generator for stimulating tissue structures via medical leads and more particularly to a device for monitoring the force applied to a proximal terminal of the medical lead by a lead terminal lock mechanism in the implantable device.

II. Discussion of the Prior Art

Implantable medical devices, such as cardiac rhythm management devices and neural stimulators typically comprise a pulse generator contained within a hermetically sealed housing and which provides electrical stimulating pulses to target tissue through a medical lead. The medical lead comprises an elongated flexible plastic lead body having one or more electrodes at a distal end thereof and a terminal pin at a proximal end. The proximal terminal may include one or more electrical contacts that are insulated from one another and connected by elongated conductors extending through the lead body and connected to the distal electrodes.

Affixed to the housing of the pulse generator is a header, typically formed from an insulating plastic, and having a longitudinally extending bore into which the proximal terminal of the medical lead may be inserted. Disposed in the longitudinal bore are one or more contacts for mating with the contact on the lead's proximal terminal. The header contacts are connected by feed through wires, which extend through hermetic seals into the interior of the housing where they connect to the electronic circuitry comprising the pulse generator.

To prevent the lead's proximal terminal from moving within the lead receiving bore of the header, a lead lock is generally provided. One form of lead lock typically comprises a metal or plastic block captured in the lead receiving bore of the header, where the block includes a bore coaxially aligned with the lead receiving bore in the header. A transverse threaded bore is formed that intersects with the longitudinal bore in the block. A setscrew is fitted into the threaded bore and is intended to be tightened against a proximal end portion of the medical lead's terminal pin when inserted into the header to thereby prevent longitudinally directed forces on the lead from pulling the terminal pin free from the pulse generator's header.

It may happen, however, that an implanting physician may fail to adequately advance the setscrew with a sufficient force to hold the lead terminal in place. Such an event can result in a failure of the tissue stimulating device to properly function and, of course, is to be avoided.

A need, therefore, exists for a way of indicating whether a lead lock mechanism in the header of an implantable tissue stimulating device has been engaged so as to positively lock the proximal terminal of a medical lead in place. The present invention meets that need.

SUMMARY OF THE INVENTION

In accordance with the present invention there is provided a miniature strain gauge or force sensor operatively positioned within the header of an implantable tissue stimulating device to measure the amount of force applied to the proximal terminal of a medical lead by the lead lock mechanism employed in the header. The terminals of the strain gauge or force sensor are connected to feed through wires that enter the housing of the pulse generator and connect to the electronic circuit contained within the housing, whereby a force measurement can be derived and transcutaneously transmitted to an external programmer/monitor for providing a readout of the status of engagement of the lead lock mechanism with a lead's proximal terminal pin. Thus, a direct indication of physical force being applied to a lead terminal pin is provided.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
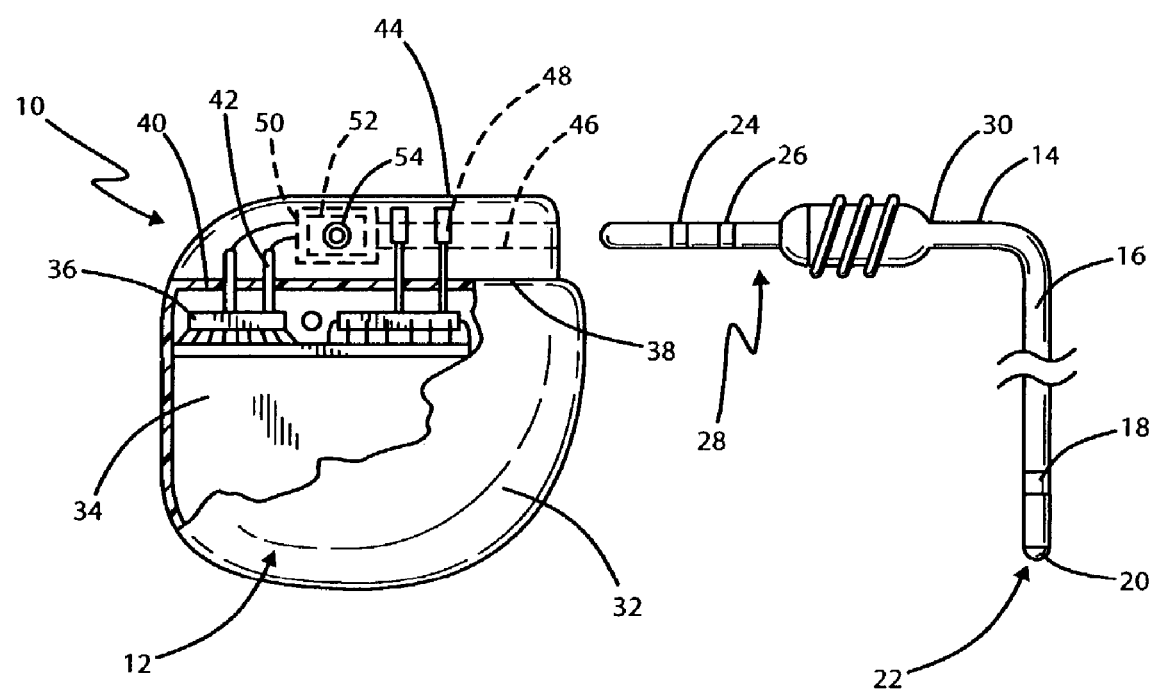
FIG. 1 is a side elevation view of an implantable tissue stimulator in which the present invention finds use.

Referring to FIG. 1, there is shown an implantable medical device incorporating the present invention. The device is indicated generally by numeral 10 and comprises an electrical tissue stimulator having a pulse generator 12 that is adapted to be connected to a target tissue site by means of a medical lead 14. The tissue stimulating device may comprise a cardiac pacemaker or a pacemaker/defibrillator, in which event the lead 14 is coupled to cardiac tissue. Alternatively, the tissue stimulating device may be used to treat chronic pain, in which event, the lead 14 may be passed into the epidural space to provide stimulation to target nerve tissue. As is known in the art, the medical lead 14 may comprise an elongated, flexible plastic lead body 16 having one or more electrodes 18, 20 disposed at or near the distal end 22 of the lead and electrical conductors (not shown) extend through the lead body 16 to connect the distal electrodes to contacts 24, 26 on a lead terminal 28 disposed at the proximal end 30 of the lead body.

The pulse generator 12 comprises a hermetically sealed container or housing 32 commonly referred to as the "can" because fabricated from a suitable metal such as titanium. Contained within the housing 32 is a battery power supply 34 and an electronic pulse generating circuit 36 that receives its electrical power from the battery supply.

Affixed to an upper flat edge 38 of the can is a feedthrough assembly 40, many forms of which are known in the art. The feedthrough assembly 40 includes one or more wire conductors as at 42 extending through a hermetic seal where one end of the wires connects to a node of the electronic circuit 36 and the other ends of the feedthrough wires become embedded in a molded plastic header 44 affixed to the pulse generator can 32.

The header 44 includes a longitudinal bore 46 dimensioned to receive the proximal terminal 28 of the lead 14 therein. Disposed within the header 44 and concentrically aligned with the longitudinal bore 46 is one or more metal contact rings, as at 48, each being tied to a feedthrough wire in the header. These contacts are designed to mate with contact areas 24 and 26 on the medical lead's proximal terminal 28 when the terminal is inserted into the longitudinal bore 46 of the header.

In order to secure the lead terminal within the header, a locking mechanism of one type or another is utilized. One prior art approach is to provide a locking member 50 having a longitudinal bore 52 for receiving the medical lead's proximal terminal 28 therein and a threaded transverse bore intersecting the longitudinal bore and, in which a setscrew 54 may be inserted and tightened against the lead's proximal terminal, forcing it against the wall of the bore in the locking member.

Figure 2:
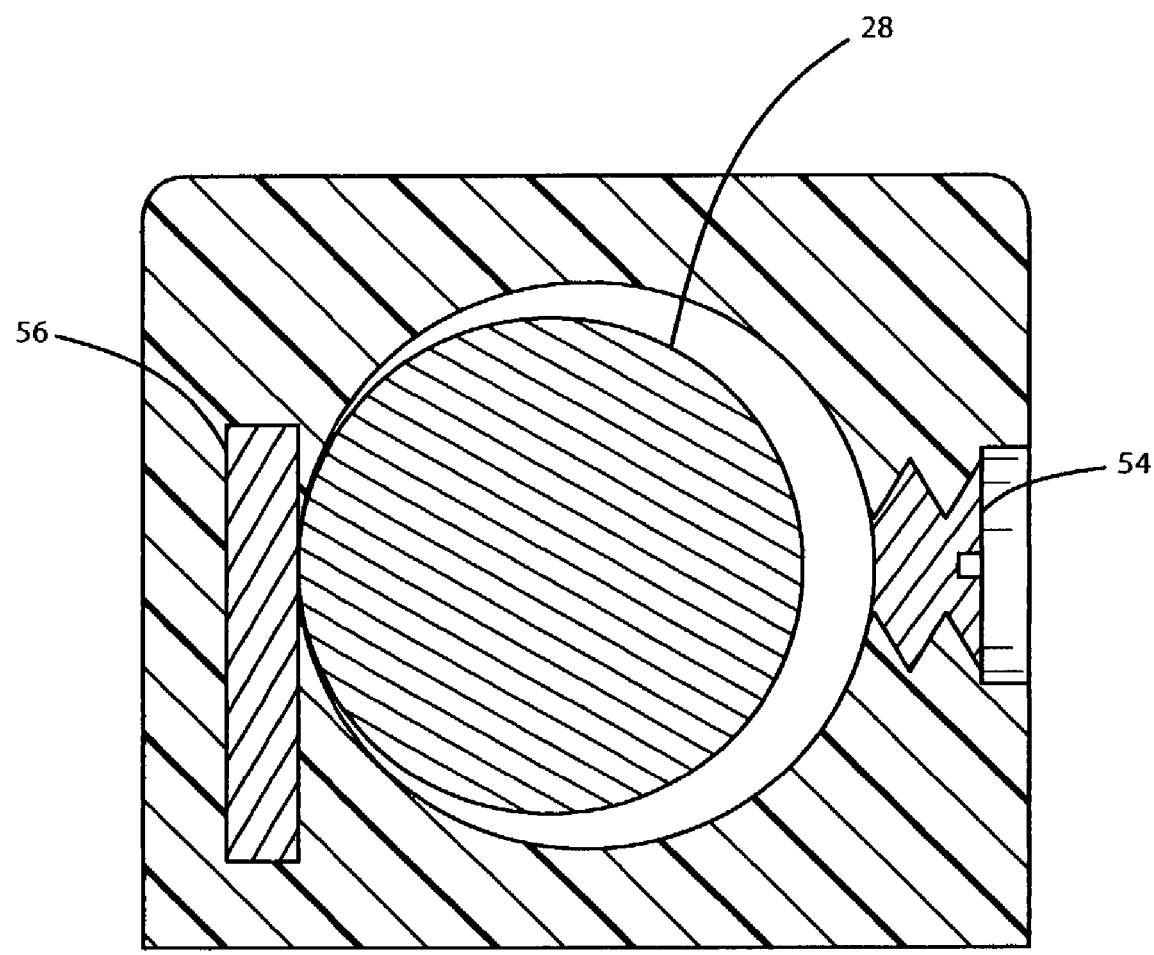
FIG. 2 is an enlarged view of a setscrew-type lead lock and incorporating a force sensor.

To insure that the setscrew is properly advanced at the time of the device implant procedure, in accordance with the present invention and as shown in FIG. 2, there is provided a force transducer in the form of a strain gauge 56 that is placed between the locking member 50 and a pocket in the header in which the locking member 50 is contained. While various forms of strain gauge or load cells are known in the art, a miniature silicon semiconductor device is preferred.

Figure 3:
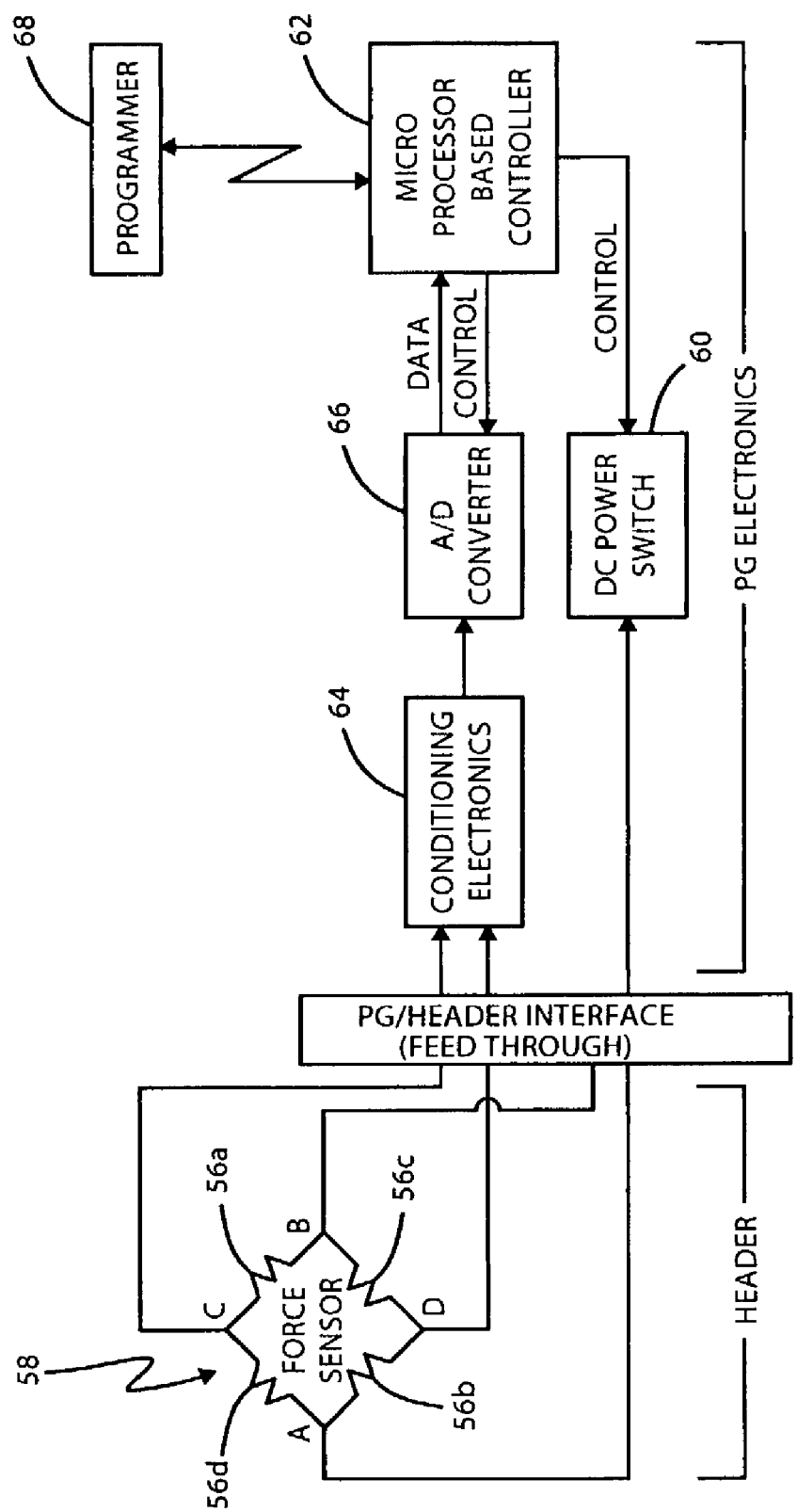
FIG. 3 is a schematic block diagram of the pulse generator incorporating the lead lock force sensor of the present invention.

As shown in FIG. 3, the load cell is constructed from four resistors 56*a* through 56*d* that are configured as a Wheatstone bridge 58. At least one of the resistors (e.g. 56*a*) is a piezoresistive element. The bridge receives its power across terminals A-B from the battery 34 in the pulse generator can 32 by way of a DC power switch 60 whose on/off state is controlled by the stimulator's microprocessor-based controller 62. In that the load cell 56 need only be interrogated infrequently and momentarily the additional load sensing circuitry of the present invention does not constitute a significant power drain on the battery.

When energized, the output from the bridge 58 is taken across bridge terminals C-D and is applied to conditioning electronics 64 known in the art for amplifying and filtering the analog signal from the bridge. This analog signal is, in turn, applied to an analog-to-digital converter 66 whose operation is also controlled by the microprocessor-based controller. A digitized output proportional to force applied to the load sensors is delivered to a "data" input terminal of the microprocessor-based controller. The implantable tissue stimulating device 10 will also preferably include a telemetry link of known design to those skilled in the art relating to implantable stimulators whereby data can be transcutaneously exchanged between the implanted device 10 and an external programmer 68.

In operation, the implanting physician will surgically create a pocket beneath the patient's skin in a predetermined location for receiving the implant 10 therein. The medical lead 14 will then be placed so that its distal electrode(s) 18, 20 will be in physical contact with target tissue. The lead body is routed so that the proximal terminal can be inserted into the longitudinal bore of the device's header. When properly inserted, the electrical contacts 24, 26 on the proximal terminal will mate with contact rings 48 in the header and the proximal end portion 28 of the terminal is inserted into the lead lock mechanism. At this time, the load resistors 56*a*-56*d* may not yet be registering an applied compressive force and the Wheatstone bridge 58 shown in FIG. 3 will be balanced. The output voltage corresponding to the balanced condition will be amplified and filtered by the conditioning electronics 64 and converted to a digital value where it is thereupon compared to a predetermined threshold by the microprocessor-based controller 62. A resulting output is thereupon provided, via the telemetry link, to the external programmer 68 and an indication given that the locking mechanism in the header 44 is not yet secured.

In the case of a locking mechanism having a setscrew 54, as illustrated in FIG. 2, the physician will advance the setscrew against the terminal pin 28, pressing the terminal pin against the load resistors 56*a*-56*d*, thereby unbalancing the bridge and creating a different analog output proportional to the compressive force being applied to the load cell elements. This analog signal is amplified and filtered and then converted to a digital quantity by the A/D converter 66 such that digital data proportional to the force being applied is conveyed to the microprocessor-based controller 62, causing a message to be telemetered to the external programmer for informing the physician of the amount of force being exerted on the terminal pin by the setscrew.

During routine patient follow-ups, the physician's programmer 68 may be used to send a signal to the implant device to activate the DC power switch 60 and obtain a read-out from the force sensor bridge 58 to determine whether there has been any appreciable change in the locking force being applied to the lead's proximal terminal.

In the case of implantable pacemaker/defibrillators, the header may contain more than one longitudinal bore for accommodating a plurality of lead terminals. Each of these bores may include a lead lock mechanism and a force sensor interconnected so as to share feedthrough wires, thereby minimizing the number of feedthrough wires required. It is further contemplated that the load cell elements may share feedthrough wires associated with the connector rings 48 that are arranged to mate with the electrical contacts 24, 26 on the proximal terminal of the lead where time multiplexing is provided by the microprocessor-based controller so that the force determination does not interfere with the functioning of the tissue stimulator.

It will be seen that the Wheatstone bridge 58 measures the contact force exerted on the lead terminal pin by the physical restraining mechanism (e.g., setscrews, retaining clips, etc.). The processor compares the force derived from the sensor with a minimum force threshold. The processor then decides if a lead has sufficient contact force to make good electrical and physical contact between the lead contacts 24, 26 and the contact rings 44 within the header bore 46. In this way, leads that are not inserted properly into the device ports are detected at the time of implant. This prevents unnecessary surgeries to tighten setscrews or reinsert leads to establish sufficient contact force with multiple contact mechanisms. The physician receives positive confirmation from the programmer that the tissue stimulating device/lead interface has physical and electrical integrity.

If desired, a second force sensor can be placed against the end to the lead bore in the header to be impinged upon by the end of the lead terminal pin when fully inserted into the lead bore 46 and thereby indicate that the lead terminal has, in fact, been fully seated within the device's handle.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In an implantable medical device comprising a hermetically sealed housing containing an electronic circuit, a header affixed to the housing and having at least one lead terminal receiving bore formed therein, a lead lock member having a longitudinal bore adapted to receive a proximal end portion of a medical lead terminal inserted into the lead terminal receiving bore, a threaded transverse bore intersecting the longitudinal bore of the lead lock member and a setscrew contained in the threaded bore for locking the lead terminal lead lock member, the improvement comprising:
   (a) a force sensor disposed in the header for producing a signal indicative of the force applied to the lead terminal by said setscrew; and
   (b) a feed through having conductors connecting the force sensor to a node of the electronic circuit.

2. The implantable medical device of claim 1 wherein the force sensor comprises a Wheatstone bridge measuring circuit.

3. The implantable medical device of claim 1 wherein the force sensor comprises a semiconductor wafer exhibiting a piezoresistive property.

4. The implantable medical device of claim 1 wherein the force sensor is disposed on the lead lock member in general alignment with the transverse bore.

5. The implantable medical device of claim 1 wherein the electronic circuit includes means for periodically applying power to the force sensor.

6. The implantable medical device as in claim 5 wherein the electronic circuit includes a telemetry link for transmitting data derived from the force sensor to an external programmer for the medical device.

7. The implantable medical device as in claim 5 wherein said means comprises a dc power switch controlled by a programmable microprocessor.

8. The implantable medical device as in claim 1 and further including a plurality of contacts in the lead terminal receiving bore adapted to mate with contacts on said medical lead terminal, said contacts in the lead terminal receiving bore being connected to conductors of the feed through.

9. The implantable medical device of claim 8 wherein the force sensor connects to said conductors of the feed through that are connected to the contacts in the lead receiving bore.

10. The implantable medical device as in claim 9 wherein the electronic circuit includes a telemetry link for transmitting data derived from the force sensor to an external programmer for the medical device.

11. An implantable tissue stimulator comprising:
    (a) a pulse generator incorporating an electronic circuit contained within a hermetically sealed housing and a header affixed to an exterior of the housing, the header having a longitudinal bore adapted to receive a proximal terminal of a tissue stimulating lead therein, the header including a contact ring and a lead locking member within the longitudinal bore, the contact ring being connected to the electronic circuit by a feed through conductor; and
    (b) a force sensor operatively coupled to the lead locking member and to the electronic circuit for providing an indication of a force exerted by the lead locking member on the proximal terminal of the tissue stimulating lead when the proximal terminal is inserted into the longitudinal bore.

12. The implantable tissue stimulator as in claim 11 wherein the lead locking member comprises
    (a) a block of material having a longitudinal bore coaxially aligned with the longitudinal bore in the header and a threaded transverse bore intersecting with the longitudinal bore in said block of material; and
    (b) a set screw fitted into the threaded transverse bore.

13. The implantable tissue stimulator as in claim 12 wherein the force sensor is disposed within the longitudinal bore in the block of material in general alignment with the threaded transverse bore.

14. The implantable tissue stimulator of claim 11 wherein the force sensor comprises a strain gauge.

15. The implantable tissue stimulator of claim 14 wherein the strain gauge comprises a Wheatstone bridge having at least one leg of the bridge a piezoresistive element.

16. The implantable tissue stimulator of claim 15 wherein the Wheatstone bridge is connected to the electronic circuit by feed through conductors.

17. The implantable tissue stimulator of claim 11 wherein the electronic circuit includes a telemetry link for transmitting data derived from the force sensor to an external programmer for the tissue stimulator.

* * * * *